US010849408B2

(12) United States Patent
Skwarek

(10) Patent No.: US 10,849,408 B2
(45) Date of Patent: Dec. 1, 2020

(54) VIRTUAL HAIR CONSULTATION

(71) Applicant: Alison M. Skwarek, Burr Ridge, IL (US)

(72) Inventor: Alison M. Skwarek, Burr Ridge, IL (US)

(*) Notice: Subject to any disclaimer, the term of this patent is extended or adjusted under 35 U.S.C. 154(b) by 2 days.

(21) Appl. No.: 16/072,029

(22) PCT Filed: Jan. 23, 2017

(86) PCT No.: PCT/US2017/014503
§ 371 (c)(1),
(2) Date: Jul. 23, 2018

(87) PCT Pub. No.: WO2017/127784
PCT Pub. Date: Jul. 27, 2017

(65) Prior Publication Data
US 2019/0035163 A1    Jan. 31, 2019

Related U.S. Application Data

(60) Provisional application No. 62/281,346, filed on Jan. 21, 2016.

(51) Int. Cl.
*A45D 44/00* (2006.01)
*G06T 19/20* (2011.01)
*G06Q 30/06* (2012.01)

(52) U.S. Cl.
CPC ....... *A45D 44/005* (2013.01); *G06Q 30/0643* (2013.01); *G06T 19/20* (2013.01); *A45D 2044/007* (2013.01)

(58) Field of Classification Search
None
See application file for complete search history.

(56) References Cited

U.S. PATENT DOCUMENTS

| 4,872,056 | A  | * | 10/1989 | Hicks ............... G06T 11/00 |
| | | | | 348/584 |
| 8,977,389 | B2 | | 3/2015 | Witchell et al. |
| 9,058,765 | B1 | * | 6/2015 | Mallick ............. G06F 3/0482 |
| 2004/0239689 | A1 | * | 12/2004 | Fertig ............... A45D 44/005 |
| | | | | 345/641 |
| 2005/0251463 | A1 | * | 11/2005 | Nagai ............... A45D 44/005 |
| | | | | 705/26.1 |
| 2005/0256733 | A1 | * | 11/2005 | Nagai ............... A45D 44/005 |
| | | | | 705/1.1 |

(Continued)

OTHER PUBLICATIONS

International Search Report and Written Opinion dated Apr. 6, 2017 for PCT/US2017/014503.

*Primary Examiner* — Justin P. Misleh
(74) *Attorney, Agent, or Firm* — Wentsler LLC

(57) ABSTRACT

Provided are a method and apparatus of generating a preview of a customizable hairstyle on an image of a client. The method includes receiving image data that is to be processed by a computer processor to generate the image of the client. An existing hairstyle of the client's is prepared as a virtual representation of the client's actual hair to appear in the image and render the virtual representation of the existing hairstyle customizable. Starting with the existing hairstyle appearing in the image of the client, a custom hairstyle is created to appear in the image of the client by modifying the existing hairstyle in the image.

17 Claims, 11 Drawing Sheets

(56) References Cited

U.S. PATENT DOCUMENTS

| | | | |
|---|---|---|---|
| 2007/0107744 A1 | 5/2007 | Dilbeck, Jr. et al. | |
| 2007/0184415 A1* | 8/2007 | Sasaki | A45D 44/005 434/100 |
| 2007/0265867 A1 | 11/2007 | Lin | |
| 2009/0046891 A1* | 2/2009 | Ikeda | A45D 44/005 382/100 |
| 2011/0115786 A1 | 5/2011 | Mochizuki | |
| 2012/0075331 A1* | 3/2012 | Mallick | G06T 11/001 345/594 |
| 2014/0306982 A1* | 10/2014 | Ollivier | A45D 44/005 345/589 |
| 2014/0313302 A1* | 10/2014 | Franke | A45D 44/005 348/77 |
| 2015/0021356 A1* | 1/2015 | Witchell | G01F 1/42 222/23 |
| 2015/0052008 A1 | 2/2015 | Campbell | |
| 2016/0102801 A1* | 4/2016 | Chu | F16M 11/08 248/125.7 |
| 2016/0112616 A1* | 4/2016 | Bonifer | H04N 5/2256 348/77 |
| 2016/0125624 A1* | 5/2016 | Liu | G06K 9/00281 345/593 |

* cited by examiner

VIRTUAL HAIR CONSULTATION

CROSS-REFERENCE TO RELATED APPLICATIONS

This application claims the benefit of U.S. Provisional Application No. 62/281,346, filed Jan. 21, 2016, which is incorporated in its entirety herein by reference.

BACKGROUND OF THE INVENTION

1. Field of the Invention

This application relates generally to generating and modifying virtual renderings of body features and, more specifically, to a method and apparatus for generating an editable rendering of a client's existing hair to prepare a preview of an altered hair style in view of the client's facial features.

2. Description of Related Art

Various methods have been proposed for generating a preview of a hairstyle on a computer. In most instances, a digitized photograph of the client's head is displayed by a computer terminal and various hairstyle options selected from a menu are overlaid on top of the client's head. However, the available hairstyle options conventionally used to generate such previews are static images, with fixed properties that may not fully illustrate all traits of the desired hairstyle envisioned by the client.

More recently, attempts have been made to allow certain properties of a hairstyle selected from a menu to be altered in the preview. For example, the color of a selected hairstyle overlaid on the client's photograph can optionally be changed to a variety of colors in a color palette of available hair dyes. However, such customization is limited to the fill color of the otherwise static graphic of the overlaid hairstyle. Due to limitations of computer displays this displayed color will likely deviate from the actual hair color actually provided to, and observed by the client, making visualization of the previewed hair color relative to the client's skin tone, eye color, etc. difficult. Further, the static graphic of a hairstyle is overlaid on each client's photograph without regard for client-specific attributes such as each individual client's: face size and shape, head size and shape, hair texture, hair thickness, skin tone, and/or other features of the client and the client's existing hair (prior to styling). As a result, computer displays have not been able to generate an accurate preview of a proposed hairstyle and hair color as it would appear on the client. Instead, conventional computer-generated previews have appeared much different than the actual hairstyle and hair color the client receives when viewed in relation to the client's face size and shape, head size and shape, hair texture, hair thickness, skin tone, and/or other features.

BRIEF SUMMARY OF THE INVENTION

Accordingly, there is a need in the art for a hairstyle preview method and apparatus that overcomes at least some of the limitations of conventional computer displays in previewing a hairstyle for each individual client. The present disclosure is directed toward such a method and apparatus that generates a preview of a hairstyle and hair color including a customizable rendering of the client's existing hair on a digitized photograph (3D Model) of the client. The computer-generated hairstyle is thus displayed relative to the client's own facial structure, skin tone, etc., for an improved representation of the actual hairstyle and hair color the client is to receive.

According to one aspect, the subject application involves a computer system that executes computer-executable instructions for rendering a captured likeness of a client in a virtual preview of aesthetic alterations to the client's actual hair, relative to one or a plurality of other attributes of the client that also appear in the preview. The preview can optionally allow full 360 degree rotation of the client's likeness and manipulation of the virtual representation of the client's actual hair (interchangeably referred to as the "virtual hair"), taking into consideration various other attributes captured by an image capture device, manually input into the computer system, or a combination thereof. Previewing alterations of the virtual representation of the client's actual hair, on the virtual likeness of the client exhibiting the client's visible attributes, greatly improves the ability of the computer system to accurately display hairstyling alterations based on the qualities of the user's actual hair, with the client's own likeness as a frame of reference.

For example, the computer system can support hair grouping, section selection, or both. Utilizing the virtual hair, the present technology will group the virtual hair matching the hair style and flow. The sensitivity or orientation of this grouping can be altered to allow for finer detail or more general hair groupings. From the hair groupings, a user can then select several hair groups in the preview to create a selected section for alteration, and/or alter individual hair groupings. A section of hair can be moved throughout the 3D space within the physical confines of the hair length (i.e., the virtual representation of the hair can optionally be prevented from being extended beyond the then current length of the client's hair). However, alternate embodiments can allow the virtual hair to be lengthened to preview hairstyles that would be possible if the client let his/her hair grow. Then it can be pinned/held statically to simulate a new hairstyle, or the stylist can manually hold the virtual hair in a static position as they would normally, during physical hairstyling of the client's actual hair. The latter will allow for easier application of features detailed later in this document. Once the stylist is done holding the virtual hair section, they can release the section allowing the accelerative force of gravity simulated by the computer system to be reapplied to the hair in the preview. This will cause the virtual hair section that was being held to fall naturally into place, later to be styled with virtual styling tools to achieve the client's desired look or style.

Globally or confined to hair sections, the user can apply colorings to the virtual hair, starting from the client's hair color appearing in the captured images used to generate the preview. The user can also cut the virtual representation of the hair in the preview by mapping a nonintersecting line from one vertical start point to a vertical end point. This allows the user to freely cut the virtual representation of the hair in a straight line, jaggedly, in smooth curves, etc. Once the mapping is done, the virtual representation of the hair will truncate the affected strands of the virtual hair up to the drawn line. The remaining virtual hair trimmings will be discarded or otherwise hidden from view.

At any point during the alterations, the current state of the virtual hairstyle can be saved as a snapshot. This allows several styles to be previewed during one session. The user can also undo an alteration that has been previously completed, or even revert the virtual hair to its original state.

To achieve at least some of the foregoing aspects, a pre-rendering survey is presented to serve as analytics and aid for the stylist. Portions of these surveys can be utilized to add in the rendering of the virtual hair and virtual face appearing in the preview. Length, thickness, and texture can determine the extent and type of curliness, weight, and flow of the hair, for example.

The virtual hair flow, style, length, and texture determined by the computer system can optionally be overridden and superimposed on to the virtual likeness of the client appearing in the preview. In some cases when the stylist wants to start from a particular state, the stylist can "grow" (lengthen) the virtual hair from its starting length to a length of their liking. The stylist can create a virtual hair type with attributes of color, thickness, texture, and flow tendencies. The stylist can select and edit a root layout style. From this layout style, they can then grow the virtual hair length from the roots to the desired length using a preconfigured or custom hair type. Growing the virtual hair will be done by extruding polygons that subdivide the scalp with regard to the root layout style. The definition and density is also configurable. This will allow an optimized styling flow for the virtual styling to appear in the preview generated by the computer system.

According to another aspect, the subject application involves a method of generating a preview of a customizable hairstyle on an image of a client. The method includes receiving image data that is to be processed by a computer processor to generate the image of the client. An existing hairstyle of the client's is prepared as a virtual representation of the client's actual hair to appear in the image and render the virtual representation of the existing hairstyle customizable. Starting with the existing hairstyle appearing in the image of the client, a custom hairstyle is created to appear in the image of the client by modifying the existing hairstyle in the image.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 2:
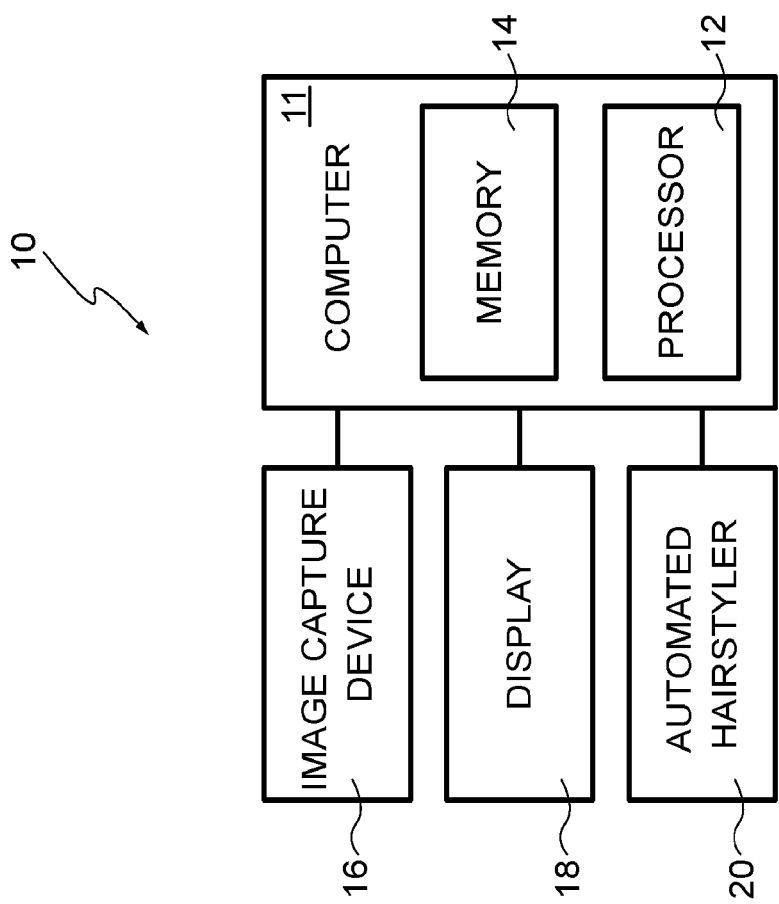
FIG. 2 is a block diagram schematically depicting various components of an illustrative computer system for generating a preview of a customizable hairstyle on an image of a client.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

FIG. 2 shows an illustrative embodiment of a computer system 10 that includes a computer 11 comprising a computer processor 12 that executes computer-executable instructions stored in a non-transitory computer-readable memory 14, such as solid-state or magnetic-disc hard disk drives, for example. When executed, the computer-executable instructions cause the computer 11 to render a captured likeness of a client in a virtual preview of aesthetic alterations to the client's actual hair, as captured by an image capture device 16, which can include one or more digital cameras for example. The aesthetic alterations appearing in the virtual preview can be based on the attributes of the client's existing hair, and optionally displayed by a display device 18 operatively connected to the computer 11 relative to one or a plurality of other attributes of the client that were captured by the image capture device 16 in the preview. The preview can optionally allow full 360 degree rotation of the client's likeness to show the hairstyle from a plurality of different vantage points, and manipulation of the virtual representation of the client's actual hair (interchangeably referred to as the "virtual hair"), taking into consideration various other attributes captured by an image capture device, manually input into the computer system 10, or a combination thereof. Previewing alterations of the virtual hair, on the virtual likeness of the client exhibiting the client's visible attributes, greatly improves the ability of the computer system 10 to accurately display hairstyling alterations based on the qualities of the user's actual hair, as they will appear on the client once actual, physical hairstyling is complete. The previewed hairstyle performed on the virtual hair can optionally be defined by data transmitted by the computer 11 to an automated hairstyling device 20 with mechanized hair cutting, coloring, drying, curling, etc. devices that can automatically reproduce the previewed hairstyle on the client, without stylist intervention, under the control of the computer 11.

Figure 1:
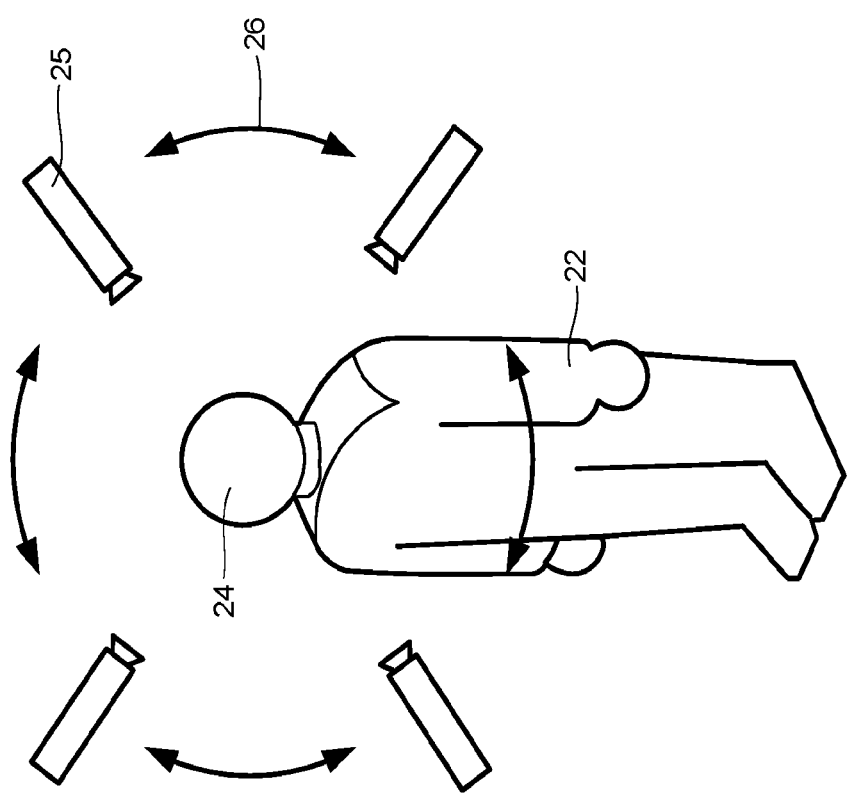
FIG. 1 is a perspective view of the creation of an illustrative imaging system that captures a virtual representation of a client's existing hair.

The method of generating the virtual representation of the client's actual hair, and subsequent hairstyling applied to that virtual hair to be displayed by a display device 18 (e.g., computer monitor, plasma and LCD television, holographic display, etc.) can begin with capturing the client's likeness, as illustrated schematically in FIG. 1. As shown, the client 22 can stand or be seated in a stationary position, and one or more digital cameras 25, video cameras, or other suitable image capture device 16 can be repositioned at a plurality of locations about the client's head region 24. According to alternate embodiments, the client 22 can rotate to provide a stationary camera 25 with each of the vantage points that would be achieved by rotating the camera(s) 25 about the client 22.

At least one, and optionally a plurality of images are captured of the head region 24 at each of the plurality of locations to capture image data that can be used to reproduce a full 360 degree image of the head region 24 as indicated by arrows 26. A suitable number of images can be taken about the head region 24 to allow those images to be stitched together by the computer 11 to assemble a three-dimensional virtual representation of the client's head region 24. This virtual representation of the client's head region 24 can then be rotated 360 degrees within the preview displayed by the display device 18 to provide a complete view of the proposed hairstyle being previewed.

Figure 3:
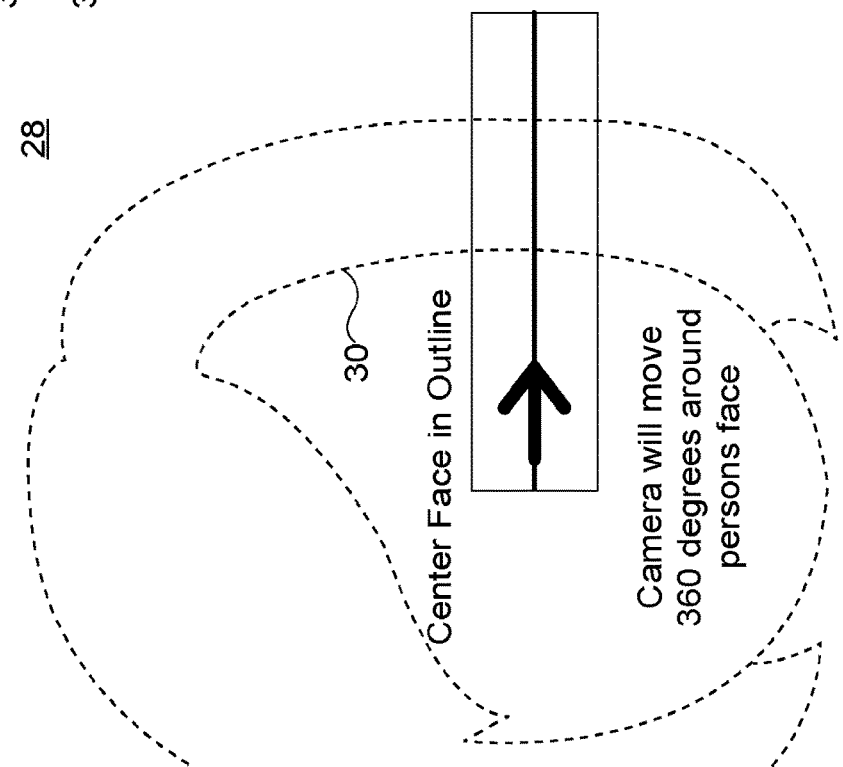
FIG. 3 shows an illustrative embodiment of an alignment interface displayed by a display device for positioning a virtual representation of a client's head and hair.

At least one of the captured images received by the computer 11 can be arranged within the interface 28 displayed by the display device 18 as shown in FIG. 3, to provide a reference point for the analysis of the virtual representation of the client's likeness. Aligning the client's face within the interface 28 provides the computer system 10 with basic information about the general vicinity in which certain landmarks are likely to appear in the image(s) being analyzed. For instance, centering the image of the client within the outline 30 in FIG. 3 suggests that the client's nose will appear within a central region of the outline 30. Likewise, the client's chin will appear towards the bottom of the outline 30, and the client's hair will be positioned towards the top of the outline 30. By centering the client's face within the outline 30, the algorithms used for recognizing certain features of the client's face and hair can be derived specifically to detect attributes of those features within the regions where they are most likely to appear, thus improving the attributes that can be recognized by the computer 11 in preparing the virtual representation of the client's hair.

One example of a suitable technique for detecting the client's face, and possibly other attributes is the Circle Hough Transform (CHT) technique. The CHT technique utilizes the Hough Transform, optionally modified to focus on oblong shapes common to human faces, as a feature extraction technique for detecting circular boundaries. The CHT technique is well adapted to identifying circular shapes in imperfect image inputs by ranking candidates in the Hough parameter space and then selecting the local maxima in a so-called accumulator matrix. Based on such an analysis, the boundary of the client's face can be roughly identified by the computer 11. Such an analysis and the accompanying drawings are not the only type of recognition application that can be utilized to recognize objects such as the client's face and other facial features, but are described herein as merely examples of the types of analysis that can be performed.

Figure 5:
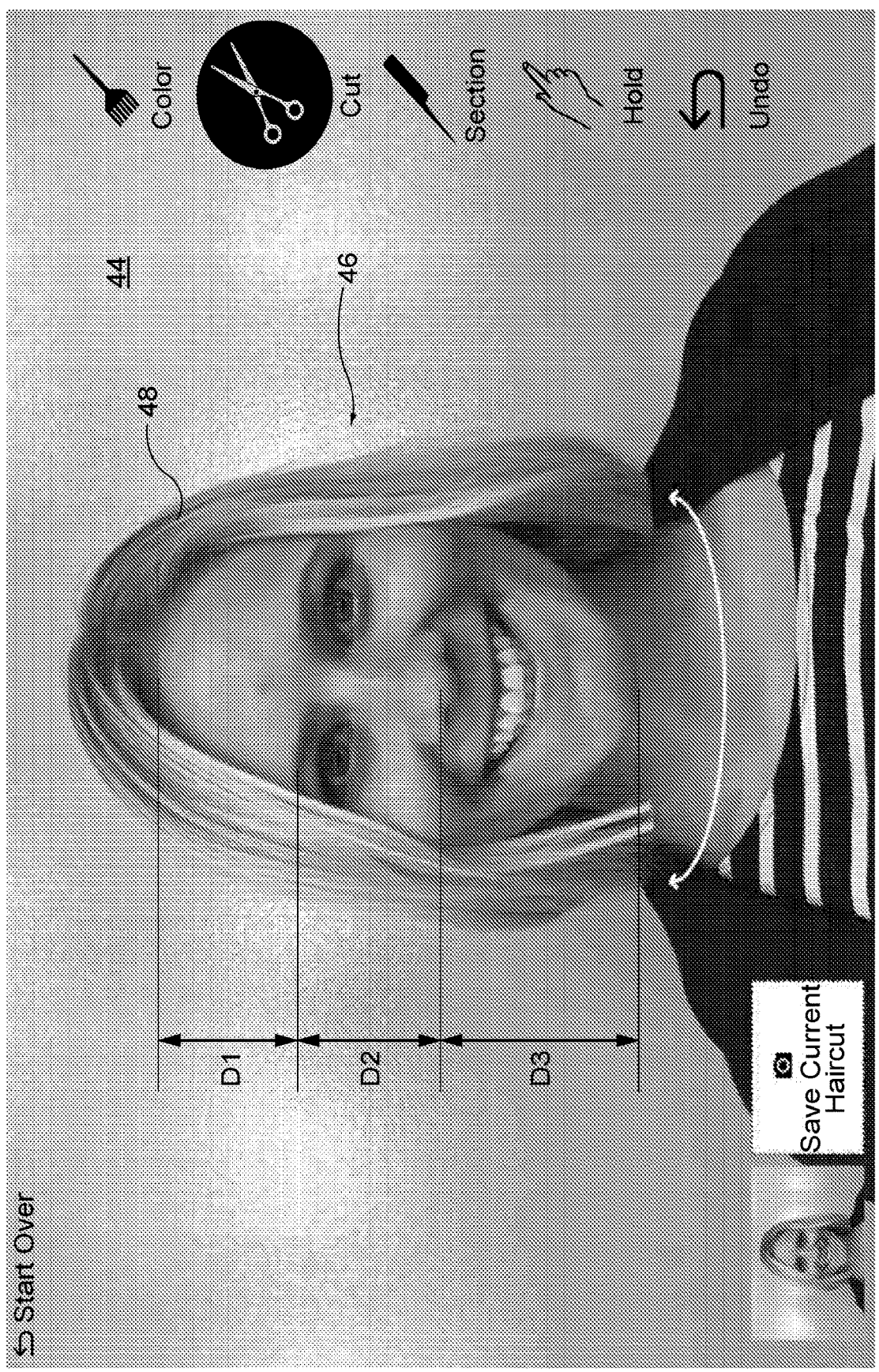
FIG. 5 is an illustrative front view of the virtual representation of the client's face and existing hair captured by an image capture device such as a camera and displayed by a display device, with facial dimension lines shown for illustrative purposes, however the facial dimension lines can optionally be displayed in the computer generated preview and optionally be made manually adjustable to fine tune the facial shape recognition.

With the client's face properly positioned and the boundary of the client's face identified by the computer 11, the method can further involve a determination of the client's facial structure based on certain landmarks. For example, the client's facial shape can be determined by measuring a distance separating certain facial features at a plurality of different locations on the client's face. As shown in the preview 44 of FIG. 5, a plurality of distances D1, D2, D3 can be measured to determine the clients facial shape. For instance, the distance D1 between a hairline of the client and an eyebrow of the client can be measured; the distance D2 between the eyebrow and a distal end of the client's nose can be measured; and the distance D3 between the end of the nose and a bottom of the client's chin can be measured. Color gradients occurring in certain regions of the client's face where the computer 11 expects the nose, chin, eyebrow, etc. to be located based on the proper positioning of the face as noted above can be used to identify the location of each facial feature used in measuring the distances D1, D2, D3. Based on the lengths of these distances D1, D2, D3, and optionally the width of the client's face at one or more locations along the height of the client's face. Previewed hairstyles generated for the client's likeness in the preview by the computer 11 can be customized according to the client's specific facial shape.

Figure 4:
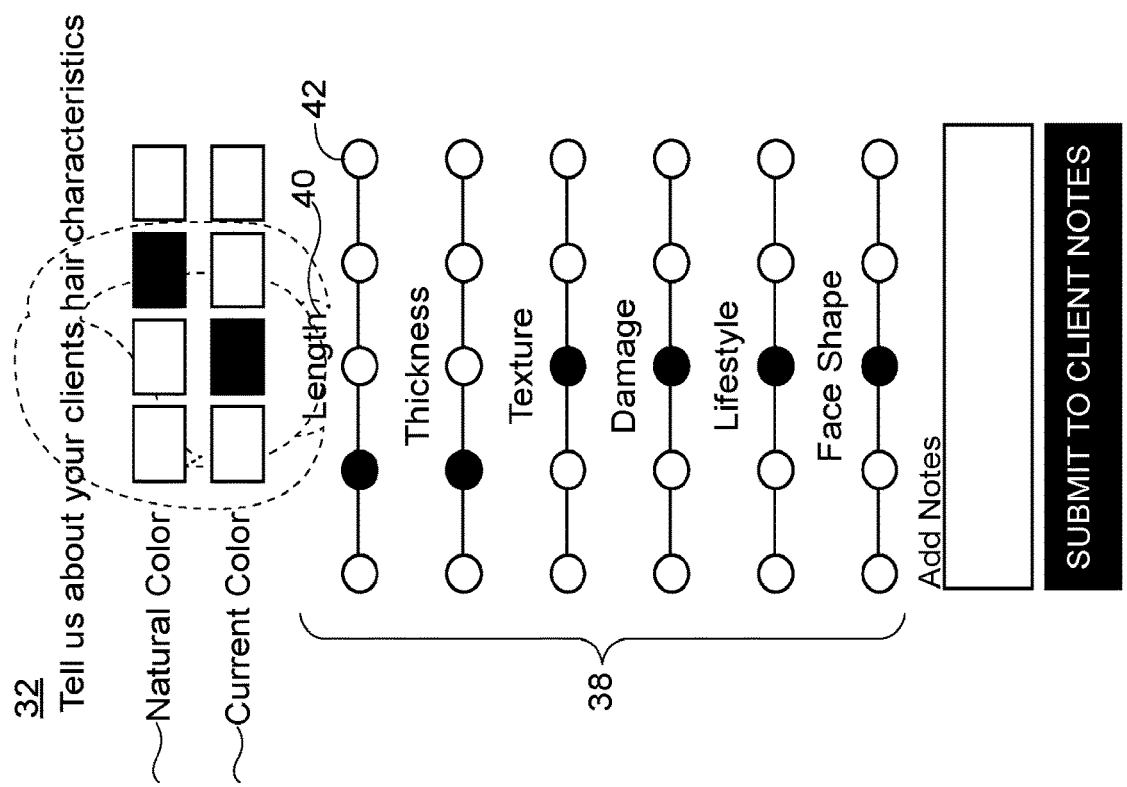
FIG. 4 shows an illustrative embodiment of a menu of manually-selectable options that allow a user to input characteristics of the client's hair, face and possibly other attributes.

In addition to positioning the image of the client's face for digital image analysis, the operator can optionally be prompted by a user interface 32 shown in FIG. 4 to manually input additional information about the client's attributes. The user interface 32 can include at least one color selection tool, and optionally a plurality of subjective ranking tools 38 that allow the operator to fine tune the attributes recognized by the computer 11 on a relative scale. For the illustrative embodiment shown in FIG. 4, a natural color menu 34 can be selected to display a full, or at least common pallet of colors from which the operator can pick the natural hair color of the client's hair, as specified by the client 22. A current color menu 36 can also be provided, allowing the client's current hair color to be manually entered into the computer system 10 if different than the natural hair color entered via the natural color menu 34 or recognized by the computer 11 from the captured images. For instance, if the client has previously colored his/her actual hair using a known hair coloring application, that known hair color can be entered via the current color pallet 36, if different than the client's natural hair color. The natural hair color selected via the natural color menu 34, the current hair color selected from the current color pallet 36, or the hair color in the captured images can appear in the preview 44 as part of the starting hairstyle to be modified.

For the embodiment shown in FIG. 4, each of the ranking tools 38 includes five fillable "bubbles" corresponding to five increments of a scale corresponding to each attribute. For the example shown in FIG. 4, the ranking tools 38 include a category to specify the length 40 of the client's hair appearing in the captured images. The five fillable bubbles 42 range from a "short" option on the far left to a "long" option on the far right. In the illustrated embodiment, the second shortest option has been selected as denoted by the filled bubble, serving to refine or confirm the recognized attributes of the client's hair from the captured images. In addition to the length category 40, the other attributes included in the interface 32 include: hair thickness (ranked from bald to full), hair texture (ranked from very fine to extremely course), hair damage (ranked from virgin to severely damage), client lifestyle (ranked from sedentary to very active), and face shape (selected from among a plurality, such as the seven basic face shapes including oval, round, square, diamond, heart, pear and oblong, for example). According to alternate embodiments, other attributes can be included in the interface 32 to input whether the client's hair appearing in the captured images has been chemically treated, whether the client's hair appearing in the images includes artificial hair extensions, and/or whether the client's existing hair differs in appearance from the client's hair appearing in the captured images, which may have been captured during a previous visit. The present system and method can utilize none, one or a plurality of the ranking tools 38 to improve the accuracy of the client's likeness to appear in the preview. Although the ranking tools 38 are shown and described as fillable bubbles for the sake of brevity to clearly explain the present technology, any suitable user interface (e.g., sliding bar scale, numerical ranking, etc.) that allows the user to input an indication of degree, ranking or other selection is within the scope of the present disclosure.

The virtual likeness 46 of the client along with the virtual hair 48 is generated by the computer 11 based on the captured images and the attributes gleaned therefrom, and optionally the manually-input data via the interface 32 of FIG. 4, to appear in the preview 44 shown in FIGS. 5-13. Rather than a static image, however, at least the virtual hair 48 is an active representation of the client's actual hair to be used as the starting point to be modified for creating the hairstyle to be presented to the client as part of the preview 44. The term "virtual hair" refers to a three-dimensional 360 degree, virtual reality version of the client's hair. In other words, "virtual hair" can be considered a virtual representation of the client's actual hair within the preview 44, with an appearance matching the client's actual, existing hair as close as practically possible in relation to the other facial attributes of the client 22 also appearing in the image, but rendered capable of modification by traditional hairstyling techniques simulated by the computer 11 in the preview 44. Thus, the virtual hair 48 of the present disclosure differs from typical graphic rendering techniques that simply fill or overlay a computer-generated graphic with a selected hair color and/or hairstyle, regardless of the attributes of the real-world object represented by that computer-generated graphic for example. According to the present example, a desired hair color may appear darker on a client having a very dark natural hair color than it would appear on a client having a blonde natural hair color. Conventional display techniques are limited to simply filling a graphic overlaid onto a photograph of a client with the desired hair color and/or hairstyle, independent of the client's actual hair color and hair characteristics. As a result, the client may be unpleasantly surprised upon having his/her hair dyed that color or cut that style only to discover that the computer display did not accurately portray how the desired hair color and/or hairstyle would appear in practice, with their natural hair color and hair characteristics as a starting point.

Figure 6:
FIG. 6 is an illustrative front view of the virtual representation of the client's face and existing hair captured by an image capture device such as a camera and displayed by a display device, with pattern lines overlaid on the client's existing hair for illustrative purposes, however the pattern lines can optionally be displayed in the computer generated preview and optionally be made manually adjustable to fine tune how accurately the pattern lines represent the flow of the client's existing hair.
Figure 7:
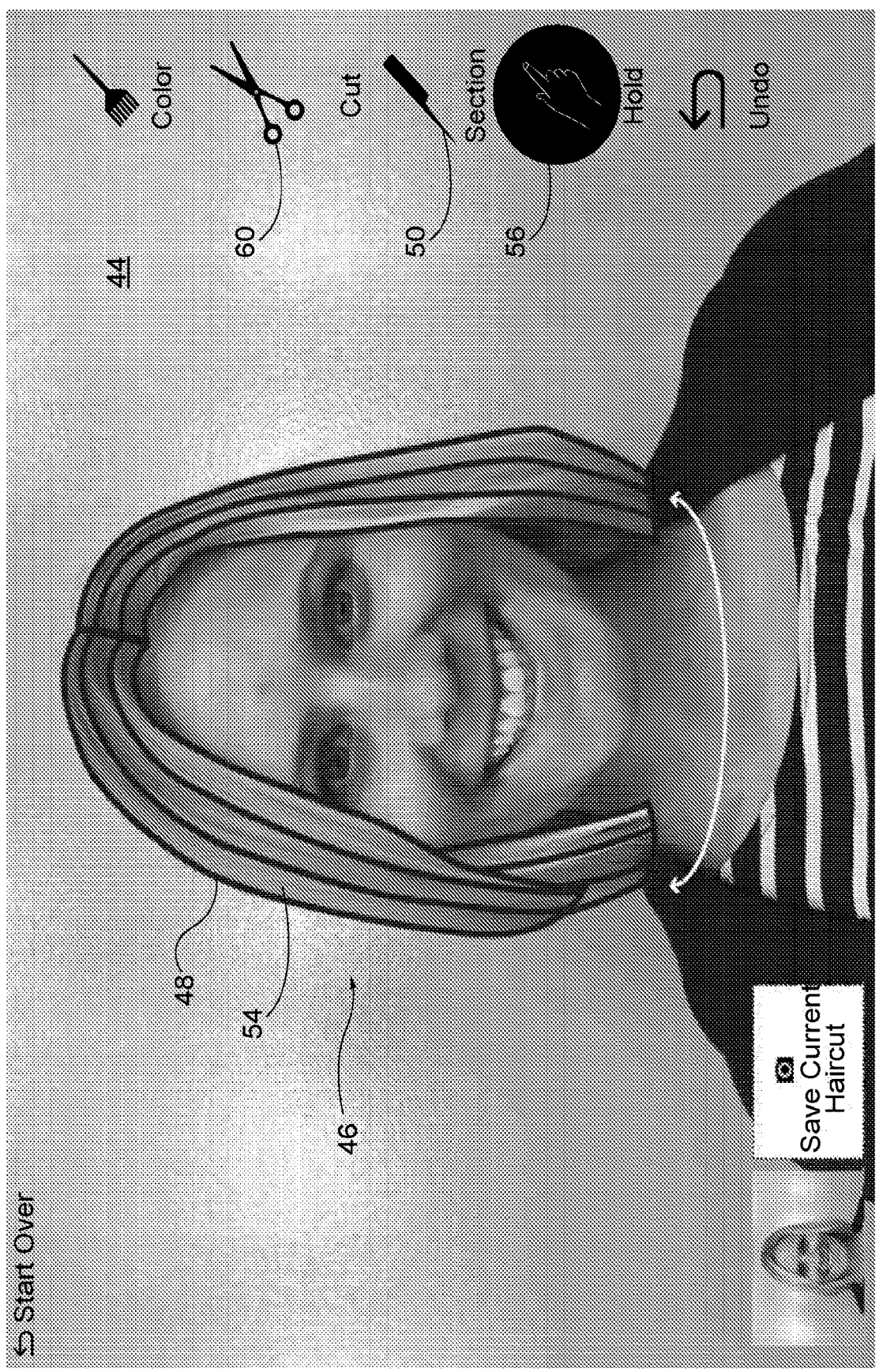
FIG. 7 shows a sub-section of the virtual representation of the client's existing hair in FIG. 6 selected in a user interface for performance of a hairstyling operation on that selected sub-section.
Figure 12:
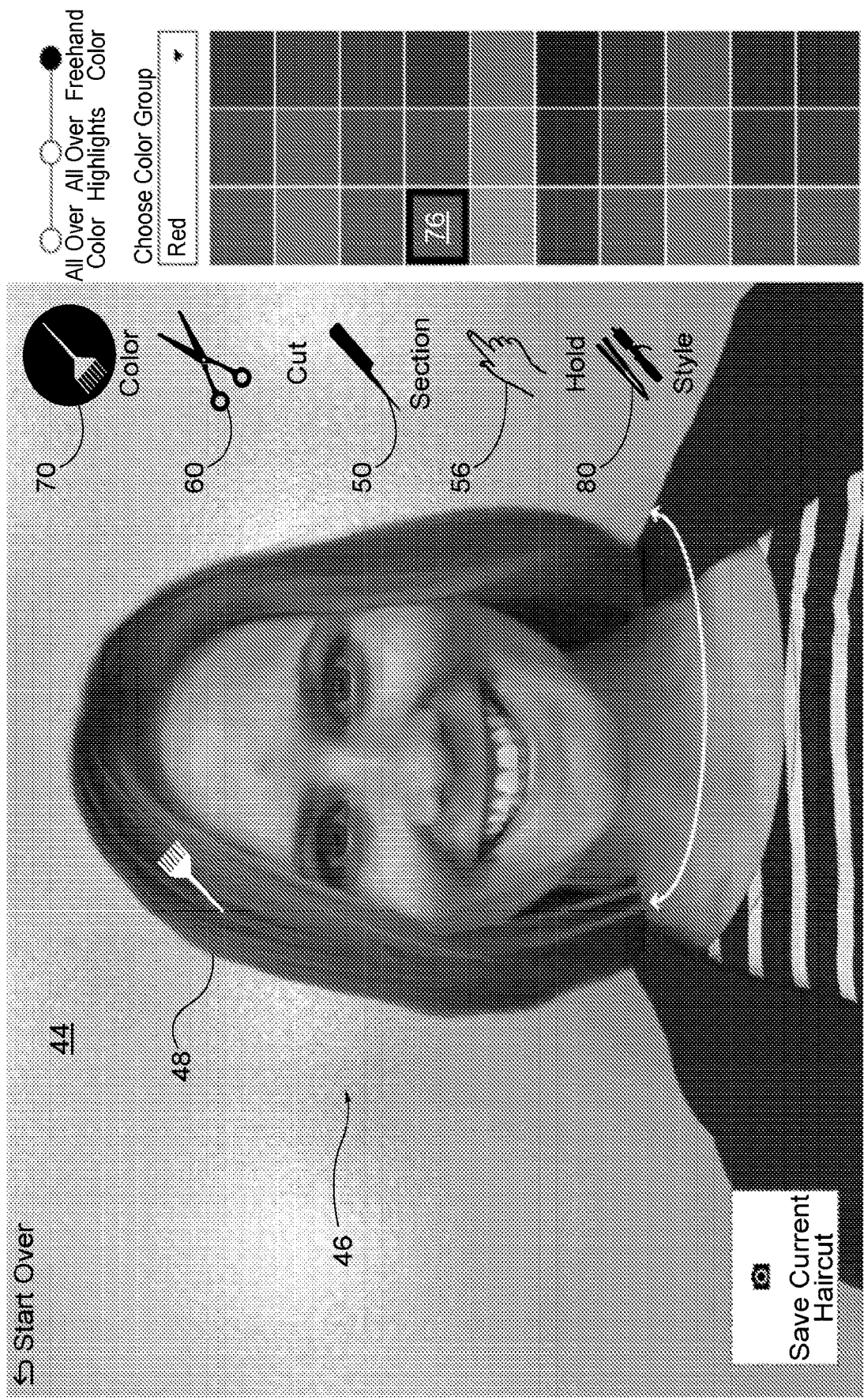
FIG. 12 is an illustrative front view of the virtual representation of the client's face and now colored hair, with a freehand coloring operation performed on a portion, but less than the entirety of the client's existing hair.
Figure 13:
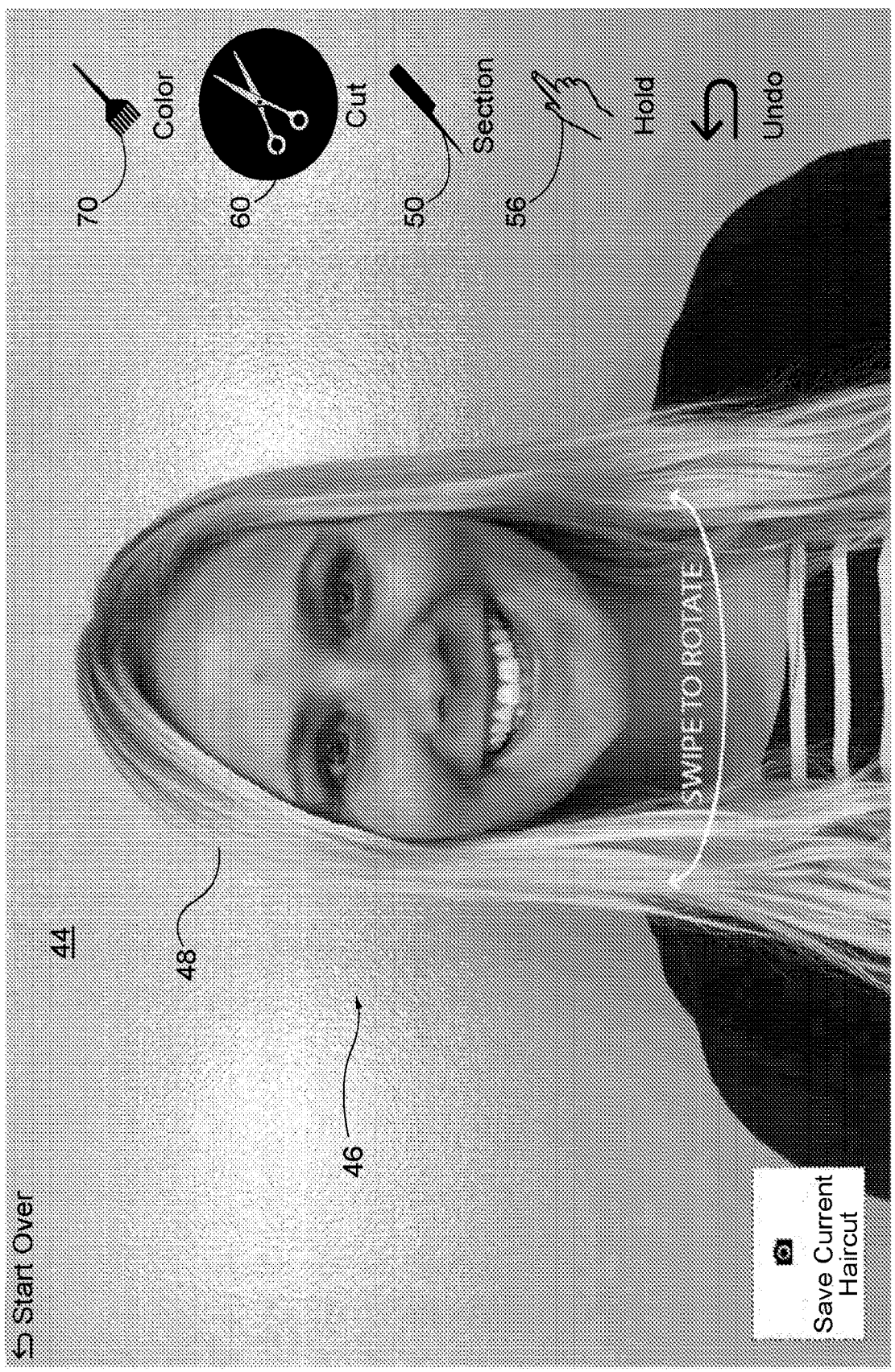
FIG. 13 is an illustrative front view of the virtual representation of the client's face and existing hair at an original length captured by an image capture device such as a camera and displayed by a computer display device, prior to the client's existing hair being trimmed to the length appearing in FIGS. 5-12.

With the virtual hair 48 generated and appearing in the preview 44, the stylist or any other operator can now simulate various hairstyling techniques on the virtual hair 48 to obtain a virtual simulation of how those techniques will translate to the client's actual hair in practice. The computer system 10 receives modifications to the virtual hair 48 through manipulation of a plurality of different hairstyling tools shown in FIGS. 5-13. For example, in FIG. 6, the operator has elected to perform a combing operation on the virtual hair 48 by selecting a sectioning tool 50 by clicking on the corresponding icon in the preview 44. In response to selecting the sectioning tool 50, the computer 11 can use color gradients, patterns, other hair attributes, or any combination thereof to generate a preliminary set of pattern lines 52 representing the hair pattern of the virtual hair 48, and/or optionally indicating a generalized, bulk direction in which hair strands extend in each of the different regions. The operator can manually select available types of lines that can be used to perform the desired direction of the cut done on the virtual hair. In FIG. 6, the available types of pattern lines 52 include diagonal lines, vertical lines, horizontal lines and pie sections that can be used to group regions of the virtual hair 48. The pattern lines can then be selected by the operator for the performance of certain hairstyling operations that are to be limited to the regions defined by the selected pattern lines, leaving the other, unselected regions unchanged. As another example, the overall length of the client's virtual hair 48 can be truncated. In FIG. 13, the original length of the virtual hair 48 is shortened from the longer-than-shoulder length to the less-than-shoulder length appearing in FIGS. 5-12 using the cutting tool 60. Following the performance of a styling operation, the pattern lines 52 for the affected region can be changed to reflect the result of the hairstyling operation. The pattern lines 52 generated by the computer based on digital image analysis of the captured images of the client can be updated through manual input by the operator using a stylus, mouse, finger on a touch screen display, or other computer pointing device to move or otherwise edit any pattern lines 52.

At least a portion of the hairstyling tools used to modify the virtual hair 48 in the preview 44 require the grouping to be modified to be separated or isolated from other groupings of the virtual hair 48, as identified by the pattern lines 52. For instance, to trim one grouping of virtual hair 48 but not a neighboring grouping to create the appearance of layers, the grouping 54 has been selected using the "hold" tool 56 in FIG. 7. To identify which grouping has been selected, the selected grouping 54 is shaded a different color than the non-selected groupings in FIG. 7, but other indicators such as unique pattern lines 52, etc., can be utilized to identify the selected group without departing from the scope of the present disclosure.

Figure 8:
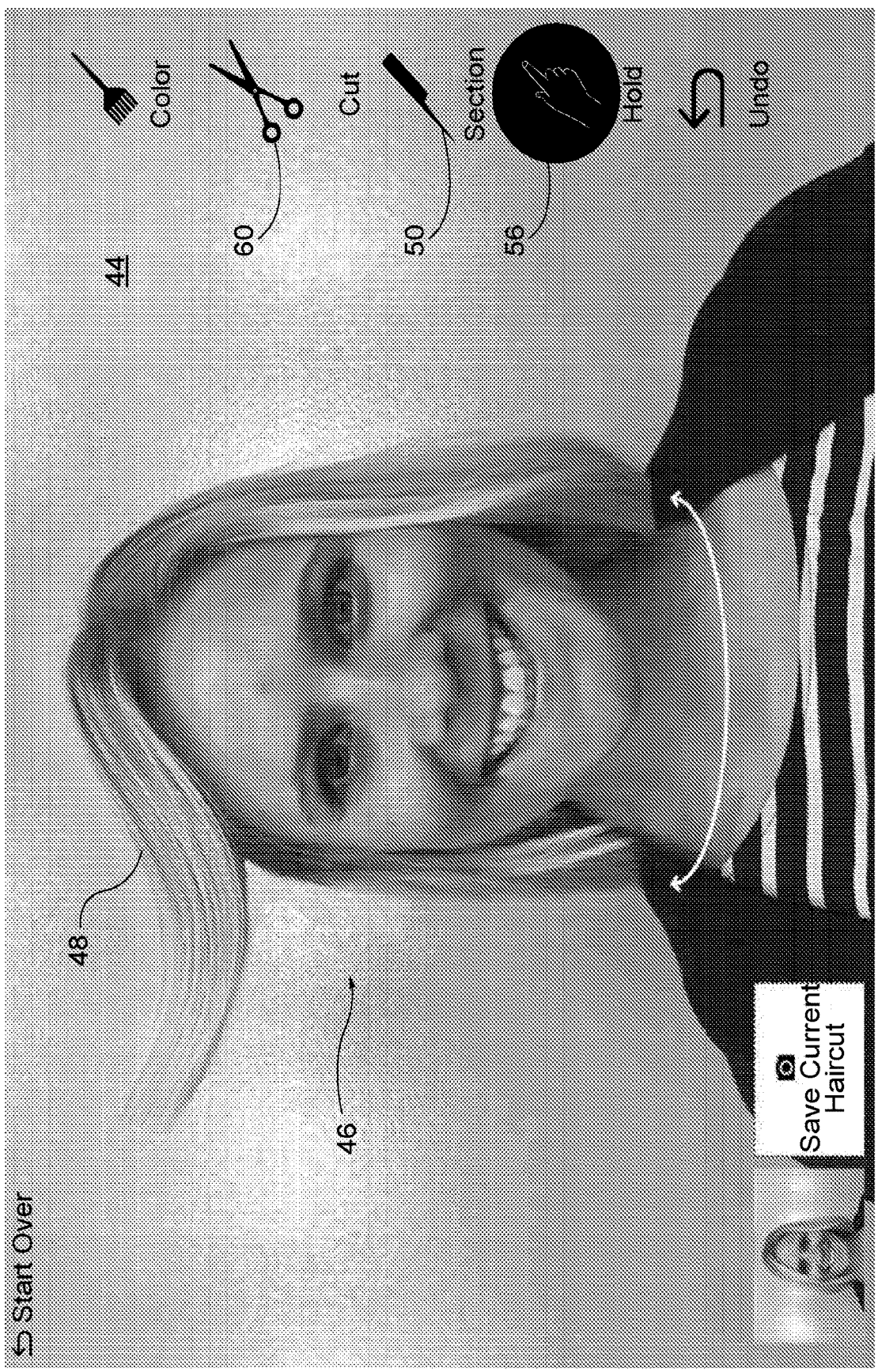
FIG. 8 shows the sub-section of the virtual representation of the client's existing hair in FIG. 7 repositioned for performance of a hairstyling operation on that selected sub-section.
Figure 9:
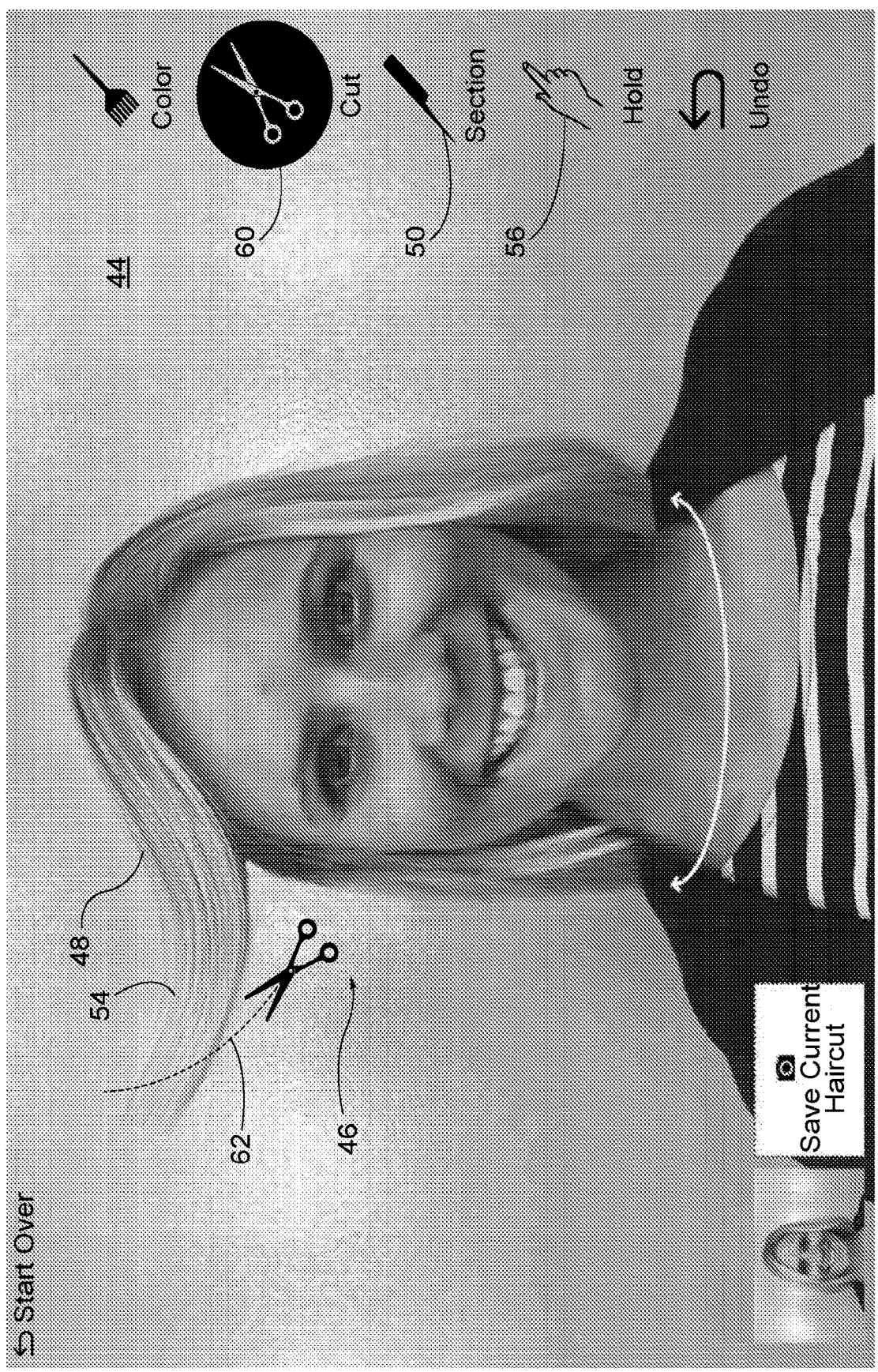
FIG. 9 shows the repositioned sub-section of the virtual representation of the client's existing hair in FIG. 8 with a cut line indicating a pattern to be cut using a cutting implement selected from a plurality of virtual hairstyling tools.
Figure 10:
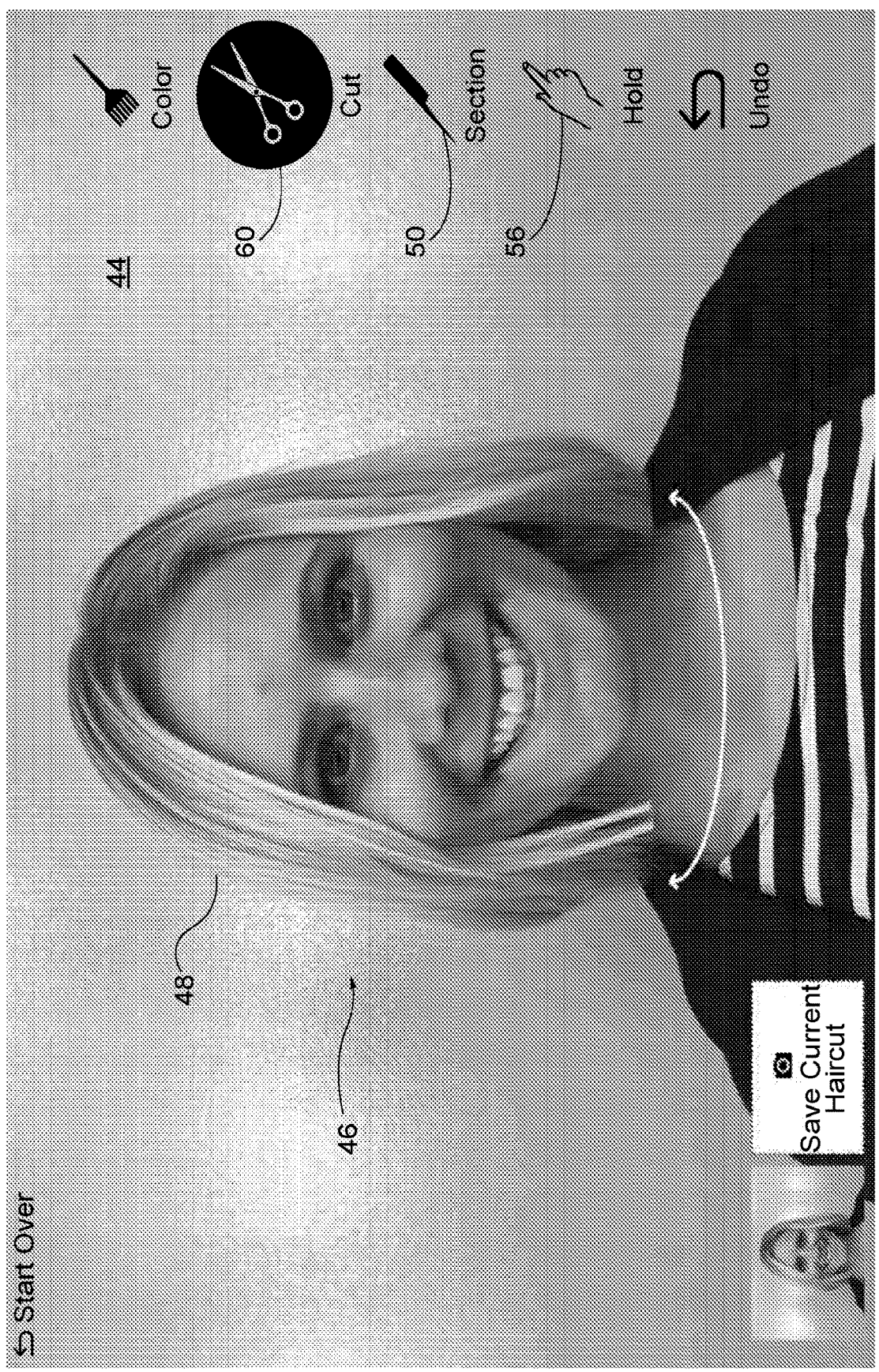
FIG. 10 shows the result of the virtual hairstyling operation performed in the view of FIG. 9 on the virtual representation of the client's actual hair.

The operator can then move the selected groupings 54 throughout the 3D space within the preview 44, optionally within the physical confines established by the hair length (i.e., the virtual representation of the hair can optionally be prevented from being extended beyond the then current length of the client's hair). However, alternate embodiments can allow the selected groupings 54 to be lengthened to preview hairstyles that would be possible if the client 22 let his/her hair grow. The effect can optionally be achieved using extensions, for example, instead of waiting for the client's own hair to grow. The moved grouping 54 can optionally be designated to be pinned/held statically within the preview 44 as shown in FIG. 8 to simulate a new hairstyle, or the stylist can manually hold the virtual hair in a static position as they would normally do during physical hairstyling of the client's actual hair. Isolating the selected grouping 54 from other, unselected groupings will help the operator limit application of a hairstyling operation to the selected grouping 54. For example, as shown in FIG. 9, the cutting tool 60 is selected to allow the operator to draw a cut line 62 marking the desired length of the selected grouping 54. The cut line 62 can be drawn straight, or include one or more waves, for example. Upon receiving confirmation of the desired cut, the computer 11 shall shorten the length of hair appearing in the selected group 54 and alter the length of pattern lines 52 for that group accordingly. Once the operator is done holding the selected grouping 54 of the virtual hair 48, the selected grouping 54 is released from the held/pinned position in the preview 44 and the accelerative force of gravity simulated by the computer system 10 causes the selected grouping 54, with the hair therein at the new length, to fall naturally into place as shown in FIG. 10. Any portions of the client's face or other attributes of the client in the preview that were previously concealed from view by the now cutaway hair can be filled in by the computer 11 using extrapolation techniques based on the shape of the client's face as determined above.

Figure 11:
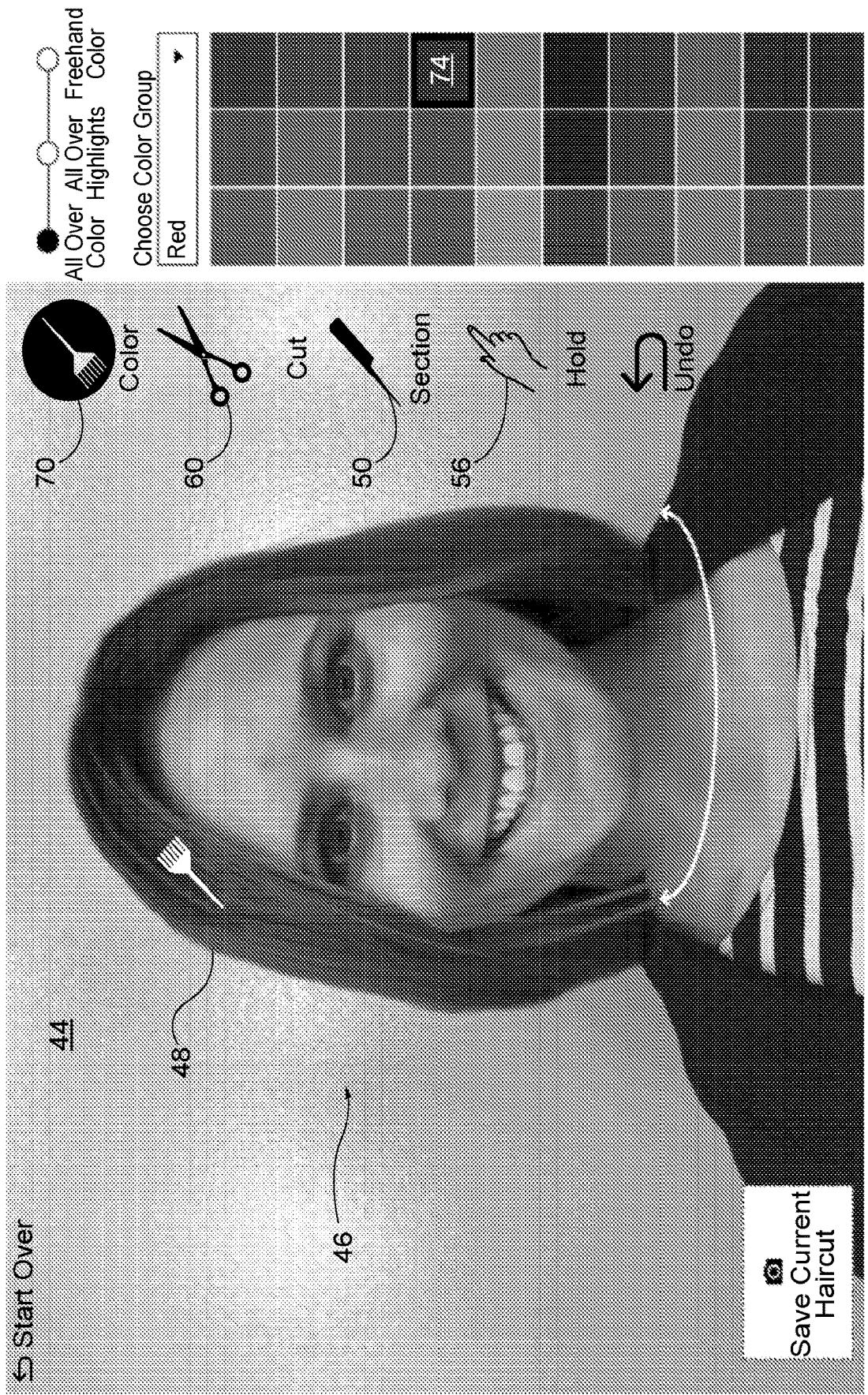
FIG. 11 is an illustrative front view of the virtual representation of the client's face and existing hair, with a bulk coloring operation performed on the client's existing hair.

Although the preceding example was described using a cutting tool 60, the present method and apparatus offers a variety of different tools available for styling the virtual hair 48. For example, the illustrative embodiment shown in FIGS. 11 and 12 provides the operator with several color tools available for modifying the color at least a portion of, and optionally all of the client's virtual hair 48. In FIG. 11, the bulk color tool 72 is selected, allowing the operator to change the bulk color of substantially all of the virtual hair 48 to a selected color 74. The virtual hair 48, optionally with the new bulk hair color, can also have portions thereof, but less than all of the virtual hair 48, be edited to include a second color 76 such as highlights, as shown in FIG. 12. For the present embodiment, the freehand tool 70 is selected to allow the operator to apply the second color 76 to only selected groupings of the virtual hair 48 to create highlights or other hair coloring effects.

Although the hairstyling tools described above relate to cutting and coloring the virtual hair 48, the embodiment shown in FIG. 12 also includes a styling category 80 of tools available to the operator to achieve other desired styling and finishing effects. For example, the styling tools can include at least one, and optionally a plurality of a hair curling implement, a hair crimping implement, a hair brushing implement, and a blow dryer, for example. Any other hairstyling tools available to a hairstylist in practice are also contemplated within the scope of the present disclosure.

The embodiments discussed above pertain to alterations performed on the virtual hair 48. However, alternate embodiments of the present method and apparatus allow the operator to select a proposed hairstyle saved in a database stored in the memory 14 of the computer 11 to be "tried on" by the client within the preview 44. Instead of, or in addition to retrieving a proposed hairstyle from such a database, a photograph of a desired hairstyle can be captured by a digital camera or other image capture device to be "tried on" by the client within the preview 44. Regardless of whether the proposed hairstyle is obtained from a database or captured using a digital camera, the proposed hairstyle can be adjusted from the condition in which it was retrieved to be specific to the client 22 appearing in the preview 44. For example, if the desired hairstyle was captured from a person having a round face, but the client has a square face, the computer 11 can modify the desired hairstyle to conform to the square face of the client. As another example, if the desired hairstyle to be shown on the client's likeness in the preview 44 has red hair and the client's natural hair color is very dark, the tint of the red color in the desired hairstyle can be adjusted to reflect how it would appear on the client. Similarly, the desired hairstyle can be adjusted in the preview 44 based on the thickness of the client's virtual hair 48, which may be thicker or thinner than the model from which the desired hairstyle was captured, to reflect how the desired hairstyle would look with the client's different hair thickness. This customization of the desired hairstyle to provide a realistic simulation of how that desired hairstyle would look on the client's head is also performed for any other hair characteristics that may differ from the desired image to the client's hair. For example, if the desired hairstyle is blond in color and the client's actual hair is very dark, the hue of that blond hair may be darkened slightly from its appearance in the desired image when shown on the client in the preview 44 to reflect dying the client's dark hair blond.

Although the examples provided above describe customizing the virtual hair 48 on top of the client's likeness in the preview 44, and the client is female in the illustrative embodiments of the preview 44 in the drawings, the present disclosure is not so limited. Rather, the client can be male, and the virtual hair to be styled in the preview 44 can be facial hair instead of, or in combination with the hair on top of the client's head without departing the scope of the present application.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:
1. A method of displaying a three-dimensional preview of a customizable hairstyle of a client on a display having a graphical user interface, based on image data of an existing hairstyle of the client, the method comprising:

receiving the image data of the existing hairstyle of the client from an image capture device, the image data representing a plurality of views of the existing hairstyle of the client captured from a plurality of different vantage points relative to the client;

displaying a three-dimensional representation of the existing hairstyle of the client on the display based on the received image data;

rendering, by a computer processor, the three-dimensional representation of the existing hairstyle of the client customizable in response to user input on the graphical user interface;

organizing, by the computer processor, the rendered three-dimensional representation of the existing hairstyle of the client into a plurality of different regions that are defined by a plurality of pattern lines, the plurality of different regions comprising at least a first region defined by a first pattern line of the plurality of pattern lines;

selecting, based on user input in the graphical user interface, the first pattern line of the plurality of pattern lines;

receiving, by the computer processor, a desired modification of the existing hairstyle of the client based on user manipulation of one or more hairstyling tools within the graphical user interface; and modifying the first region in accordance with the selected first pattern line and the desired modification of the existing hairstyle of the client to display the three-dimensional preview of the customizable hairstyle of the client.

2. The method of claim 1, wherein the image data is captured by the image capture device while a face of the client is aligned within an outline displayed on the graphical user interface adjacent to the face of the client prior to the image data being captured.

3. The method of claim 1 further comprising:
determining a facial shape of the client by measuring a distance separating facial features at a plurality of different locations on the client's face.

4. The method of claim 3, wherein the distance separating the facial features is measured:
between a hairline of the client and an eyebrow of the client;
between the eyebrow and a distal end of a nose; and
between the end of the nose and a bottom of a chin.

5. The method of claim 3 further comprising:
receiving proposed hairstyle data representing a first hairstyle to be displayed as the three-dimensional preview of the customizable hairstyle of the client; and
adjusting the proposed hairstyle based, at least in part, on the facial shape of the client for displaying the first hairstyle appropriately in the three-dimensional preview of the customizable hairstyle for the client having the facial shape.

6. The method of claim 5, wherein said receiving the proposed hairstyle data comprises receiving model hair data captured by an imaging device from a photograph of the first hairstyle.

7. The method of claim 1 further comprising:
elongating the three-dimensional representation of the existing hairstyle based on user input.

8. The method of claim 1, wherein the pattern lines further indicate a hair pattern within at least one of the different regions.

9. The method of claim 1, wherein said modifying the first region comprises altering the selected first pattern line based on the user manipulation of the one or more hairstyling tools within the graphical user interface.

10. The method of claim 9, wherein the one or more hairstyling tools within the graphical user interface comprises at least one of:
a hair cutting implement;
a hair curling implement;
a hair crimping implement;
a hair brushing implement;
a razor; and
a blow dryer.

11. The method of claim 1 further comprising:
receiving manually-input preliminary hairstyle information indicative of an un-dyed natural hair color, current hair color, thickness, density of the existing hairstyle of the client, wherein the three-dimensional representation of the existing hairstyle of the client is displayed in the natural color.

12. The method of claim 1, wherein the image data of the existing hairstyle of the client constitutes a photograph captured by a digital imaging device, and said method further comprises:
receiving preliminary hairstyle information indicating that the existing hairstyle of the client appearing in the photograph has been chemically treated, and the three-dimensional representation of the existing hairstyle of the client is displayed having a different appearance than an appearance of the existing hairstyle of the client in the photograph.

13. The method of claim 1, wherein the image data constitutes a photograph captured by a digital imaging device, and said method further comprises:
receiving preliminary hairstyle information indicating that the existing hairstyle of the client in the photograph includes an artificial hair extension, and the three-dimensional representation of the existing hairstyle of the client displayed on the display comprises an appearance that is different from an appearance of the existing hairstyle of the client in the photograph.

14. The method of claim 1 further comprising:
transmitting data indicative of the customizable hairstyle to an automated hairstyling device to control operation of the automated hairstyling device to give the client the customizable hairstyle.

15. The method of claim 1, wherein the received image data represents a full 360° virtual representation of a head region of the client, displayed on the graphical user interface as a rotatable image that can be rotated to display the full 360° virtual representation of the head region to show the existing hairstyle of the client and the customizable hairstyle from a plurality of different vantage points.

16. The method of claim 1 further comprising:
determining a thickness of the existing hairstyle by receiving a manually-input indication of perceived hair thickness;
receiving proposed hairstyle data representing a first hairstyle to be displayed as the customizable hairstyle on the graphical user interface; and
adjusting the customizable hairstyle on the graphical user interface based, at least in part, on the thickness of the existing hairstyle.

17. The method of claim 1, wherein the customizable hairstyle is displayed on the graphical user interface as facial hair of the client.

* * * * *